United States Patent [19]

Heveling

[11] Patent Number: 5,284,961
[45] Date of Patent: Feb. 8, 1994

[54] PROCESS FOR THE PREPARATION OF 6-HYDROXY-2,5,7,8-TETRAALKYL-2-(4-AMINOPHENOXYMETHYL) CHROMANS

[75] Inventor: Josef Heveling, Naters, Switzerland

[73] Assignees: Lonza Ltd., Gampel/Valais, Switzerland; Sankyo Company, Ltd., Tokyo, Japan

[21] Appl. No.: 19,587

[22] Filed: Feb. 19, 1993

[30] Foreign Application Priority Data

Feb. 21, 1992 [CH] Switzerland .................. 531/92

[51] Int. Cl.$^5$ .................................. C07D 311/58
[52] U.S. Cl. .................................. 549/407
[58] Field of Search .................................. 549/407

[56] References Cited

U.S. PATENT DOCUMENTS 5,030,601  7/1991  Michel et al. .................. 501/103

FOREIGN PATENT DOCUMENTS 0139421  6/1985  European Pat. Off. .
0207581  1/1987  European Pat. Off. .

OTHER PUBLICATIONS

J. Med. Chem., 32, (1989), pp. 421 to 428.
Shibagaki et al., Bull. Chem., Soc., Japan, 61, (1988), pp. 3283 to 3288.

Primary Examiner—Nicky Chan
Attorney, Agent, or Firm—Fisher, Christen & Sabol

[57] ABSTRACT

A novel process for the preparation of aminochromans of the general formula:

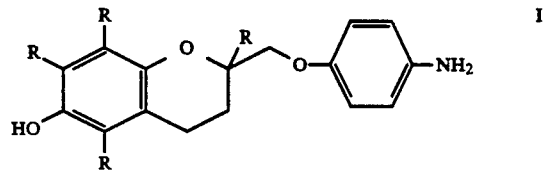

wherein R is a lower alkyl group having 1 to 4 carbon atoms. In the process, nitrochromanones of the general formula:

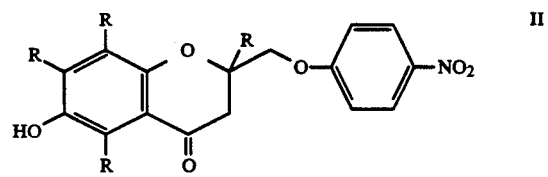

are reduced using zirconium oxide/isopropanol to give a mixture of a corresponding aminochromene:

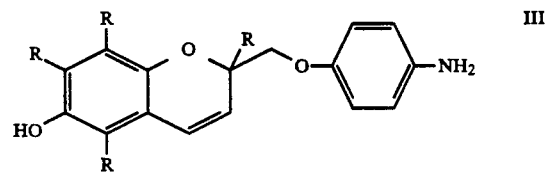

and a corresponding nitrochromene:

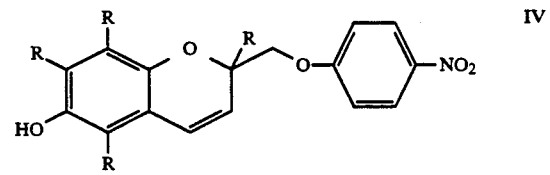

The mixture is then hydrogenated with hydrogen in the presence of a hydrogenation catalyst to give the final product. The aminochromans are important intermediates for the preparation of hypolipidaemic pharmaceuticals.

13 Claims, No Drawings

PROCESS FOR THE PREPARATION OF 6-HYDROXY-2,5,7,8-TETRAALKYL-2-(4-AMINOPHENOXYMETHYL) CHROMANS

BACKGROUND OF THE INVENTION

1. Field of The Invention

The invention relates to a novel process for the preparation of 6-hydroxy-2,5,7,8-tetraalkyl-2-(4-aminophenoxymethyl)chromans (aminochroman) of the general formula:

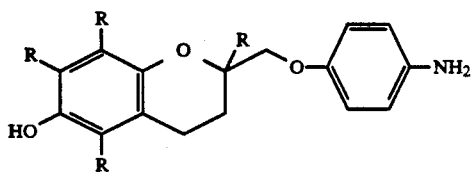

wherein R denotes a lower alkyl group having 1 to 4 carbon atoms.

2. Background Art

It is known from European Published Patent Application No. 207,581 to prepare aminochromans of the general formula I by first converting a tetraalkyl-2-(4-nitrophenoxymethyl)chroman-4-one into the corresponding chroman-4-ol using sodium borohydride, in a further step dehydrating the chroman-4-ol to the chroman-3-ene in the presence of p-toluenesulphonic acid and in the last step hydrogenating both the nitro group and the chromene double bond using a hydrogenation catalyst to give the final product. This reaction has the disadvantage that a considerable need for working up arises between the individual reaction steps, which impedes conversion of the synthesis to industrial scale. Additionally, reduction using sodium borohydride is expensive in comparison with catalytic reductions and is problematic from an ecological point of view as the resulting effluents are polluted with boron.

BROAD DESCRIPTION OF THE INVENTION

The main objective of the invention is to provide a synthesis which is simpler than the above described prior art process and stated disadvantages thereof. The main objective according to the invention is achieved by the process according to the invention.

Other objectives and advantages of the inveniton are set out herein or are obvious herefrom to one ordinarily skilled in the art.

The objectives and advantages are achieved by the process of the invention.

The invention involves a process for the preparation of 6-hydroxy-2,5,7,8-tetraalkyl-2-(4-aminophenoxymethyl)chromans of the general formula:

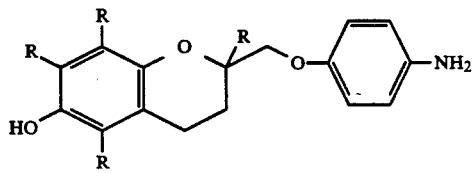

wherein R is a lower alkyl group having 1 to 4 carbon atoms. The process involves reducing a 6-hydroxy-2,5,7,8-tetraalkyl-2-(4-nitrophenoxymethyl)chroman-4-one of the general formula:

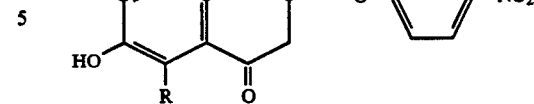

wherein R has the above-stated meaning, under pressure in the presence of a catalyst system of amorphous zirconium oxide/isopropanol to give a mixture of a 6-hydroxy-2,5,7,8-tetraalkyl-2-(4-aminophenylmethyl)-chrom-3-ene of the general formula:

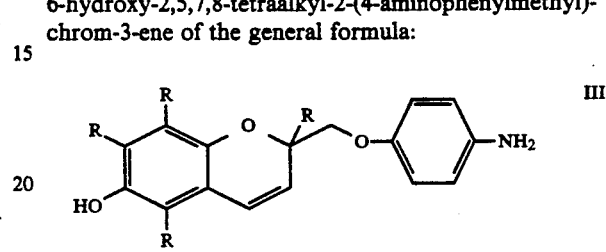

wherein R has the above-stated meaning, and a 6-hydroxy-2,5,7,8-tetraalkyl-2-(4-nitrophenoxymethyl)chrom-3-ene of the general formula:

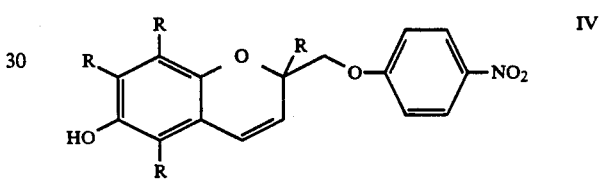

In the subsequent step, the mixture is hydrogenated using hydrogen in the presence of a hydrogenation catalyst to give the final product.

Preferably the reduction in the first step is carried out at a pressure of 1 to 50 bar and a temperature of between 80° and 220° C. More preferably the reduction in the first step is carried out at a pressure of 20 to 40 bar and a temperature of between 160° and 200° C. preferably, for the reduction, an amorphous zirconium oxide is employed which is prepared by precipitation of a zirconyl chloride solution with ammonia and subsequent drying and calcination of the precipitated zirconium oxide. Preferably the amorphous zirconium oxide is subjected to a pretreatment in a mobile inert gas atmosphere at a temperature of between 150° to 300° C. Preferably a platinum or palladium catalyst applied to an inert support is used as the hydrogenation catalyst. Preferably palladium, applied to carbon in an amount from 0.5 to 10 percent, is used. Preferably the hydrogenation is carried out at a hydrogen pressure of 1 to 20 bar and a temperature of 20° to 50° C.

These aminochromans of the general formula I are useful intermediates for the preparation of hypolipidaemic pharmaceuticals [J. Med. Chem., 32, (1989), page 421].

DETAILED DESCRIPTION OF THE INVENTION

The starting materials are 6-hydroxy-2,5,7,8-tetraalkyl-2-(4-nitrophenoxymethyl)chroman-4-ones (nitrochromanone) of the general formula:

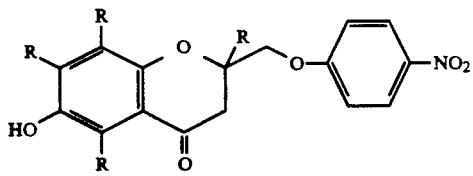

wherein R has the above-stated meaning. The compounds can be prepared, for example, from acetylhydroquinone derivatives according to European Published Patent Application No. 139,421. Preferably, 6-hydroxy-2,5,7,8-tetramethyl-2-(4-nitrophenoxymethyl)-chroman-4-one (formula II where R is CH₃) is used as the starting material.

In the first step the nitrochromanones of the formula II are reduced according to the invention in the first step in the presence of the catalyst system, amorphous zirconium oxide/isopropanol, to give a mixture of a 6-hydroxy-2,5,7,8-tetraalkyl-2-(4-aminophenoxymethyl)chrom-3-ene (aminochromene) of the general formula:

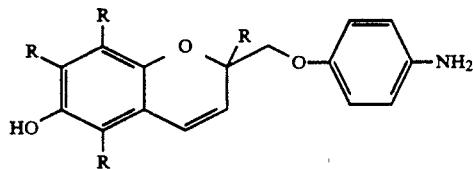

wherein R has the above-stated meaning, and of a 6-hydroxy-2,5,7,8-tetraalkyl-2-(4-nitrophenoxymethyl)chrom-3-ene (nitrochromene) of the general formula:

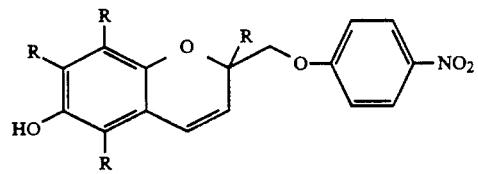

wherein R has the above-stated meaning.

The amorphous zirconium oxide employed according to the invention can be prepared in a known manner by precipitation from a zirconyl chloride solution using sodium hydroxide solution, according to Shibagaki et al., in Bull. Chem. Soc. Japan, 61, (1988), pp 3283 ff, or using ammonia, according to U.S. Pat. No. 5,030,601, and subsequent drying and calcination. Expediently, the amorphous zirconium oxides prepared have a specific surface area according to BET of between 210 and 265 m²/g. Preferably, an amorphous zirconium oxide is employed which is obtained by precipitation using ammonia.

The amorphous zirconium oxide obtained from the precipitation process is advantageously subjected to a pretreatment before its use. This is expediently carried out by treatment of the precipitated and calcined amorphous zirconium oxide in a mobile inert gas atmosphere at 150° to 300° C. over a period of 1 to 24 hours.

Expediently, the reaction in the first step is carried out by initially introducing the nitrochromanone of formula II together with the pretreated amorphous zirconium oxide in isopropanol, which functions as a reactant and solvent. If appropriate, a molecular sieve can be employed to remove water from the equilibrium. In this way, the reaction rate and the selectivity can be favorably influenced. The reaction rate can be increased by addition of a small amount of a mineral acid, such as, hydrochlorid acid. The reaction is preferably carried out with exclusion of air at pressures between, expediently, 1 to 50 bar, preferably 20 to 40 bar, and a temperature of, expediently, between 80° and 220° C., preferably 160° to 200° C. The reaction is complete after a reaction time of, as a rule, 3 to 10 hours.

The nitrochromene of formula IV and the aminochromene of formula III can be isolated from the reaction mixture in the form of a mixture after separating off the zirconium oxide catalyst and removing the solvent, the amount of nitrochromene of formula IV usually predominating and as a rule being 75 to 80 percent. However, it is also possible to use the reaction solution containing the mixture of nitrochromene of the formula IV and aminochromene of the formula III directly for the subsequent step after separating off the zirconium oxide catalyst.

In the subsequent step, the mixture of the nitrochromene of formula IV and the aminochromene of formula III is hydrogenated to give the final product of formula I using hydrogen in the presence of a hydrogenation catalyst. Suitable hydrogenation catalysts are expediently noble metal catalysts, such as, palladium or platinum applied to inert support materials, such as, carbon or alumina. Preferably, the hydrogenation is carried out using a palladium catalyst, applied in an amount from 0.5 to 10 percent to carbon as an inert support. The hydrogenation is expediently carried out at a hydrogen pressure of 1 to 20 bar, preferably 5 to 10 bar, and a temperature of 20° to 50° C., preferably at room temperature. As a rule, the uptake of hdyrogen is complete after 0.5 to 6 hours, after which the final product, of formula I, can be isolated in a simple manner by separating off the catalyst and removing the solvent.

EXAMPLES

Preparation of the amorphous zirconium oxide
(Preparation A)

Zirconyl chloride octahydrate (ZrOCl₂.8H₂O) was dissolved in water. The slight turbidity was filtered off, and the solution was adjusted to a content (ZrO₂) of 50 g/l using deionized water. Technical ammonia (about 25 percent) was diluted to a concentration of 10 percent using deionized water. 2.5 l of deionized water was introduced into a reaction vessel. The zirconyl chloride solution and the ammonia solution were added in a controlled manner while stirring at 8000 rpm. The rate of addition of the ZrO₂ solution was 50 ml/min. The ammonia solution was added in such a way that it was possible to maintain a pH of 7.0+0.2 during the resultant precipitation. The solids content of the suspension was kept at about 1 percent by addition of deionized water. After the precipitation was complete, the solid was separated off by filtration. The filter cake was washed several times using ammoniacal water until the Cl content had been reduced to 0.05 percent. The filter cake was then dried at 100° C., suspended once more, filtered and dried again. Finally, the resulting ZrO₂ powder was calcined at 300° C. for 8 hours. The resulting ZrO₂ was radiographically amorphous and had a specific surface area according to BET of 240 m²/g.

EXAMPLE 1

(a) Process for the preparation of a mixture of 6-hydroxy-2,5,7,8-tetraalkyl-2-(4-aminophenoxymethyl)chrom-3-ene (aminochromene, III) and 6-hydroxy-2,5,7,8-tetramethyl-2-(4-nitrophenoxymethyl)chrom-3-ene (nitrochromene, IV)

2.0 g (5.4 mmol) of 6-hydroxy-2,5,7,8-tetramethyl-2-(4-nitrophenoxymethyl)chroman-4-one (II) was introduced into an autoclave with exclusion of air together with 5 g of amorphous zirconium oxide (prepared as in Preparation A above and pretreated for 2 hours at 200° C. with the passage of argon), 100 g of isopropanol (dried using molecular sieve 4 Å), 1.0 g of molecular sieve 4 Å (pretreated for 3 hours at 300° C. with passage of argon) and 2.5 ml of concentrated hydrochloric acid. After flushing several times with nitrogen, the mixture was heated to a temperature of 190° C. at a pressure of 10 bar while stirring at 750 rpm. The pressure rose during the course of this to 27 to 31 bar. After 6 to 7 hours, the reaction mixture was cooled to room temperature, the amorphous zirconium oxide was separated off and the solvent was evaporated off. In this way, 1.9 of a mixture which contained 57.5 percent of nitrochromene (IV) and 16.3 percent of aminochromene (III) was obtained.

(b) Process for the preparation of 6-hydroxy-2,5,7,8-tetramethyl-2-(4-aminophenoxymethyl)chroman (I)

1.9 g of the mixture obtained in Example 1(a) and having a content of 73.8 percent was introduced into an autoclave with 0.4 g of a palladium-on-carbon catalyst (5 percent Pd/C) in 60 ml of toluene. After flushing several times with nitrogen and then with hydrogen, the mixture was stirred at 750 rpm at a hydrogen pressure of 8 bar and at room temperature (24° to 27° C.) for 3.5 to 4 hours. The reaction mixture was then freed from the catalyst. The solvent was evaporated off. The crude mixture (1.8 g) contained the title product in a yield of 74.3 percent.

EXAMPLE 2

Process for the preparation of 6-hydroxy-2,5,7,8-tetramethyl-2-(4-aminophenoxymethyl)chroman (I)

2.0 g (5.4 mmol) of 6-hydroxy-2,5-,7,8-tetramethyl-2-(4-nitrophenoxymethyl)chroman-4-one (II) was introduced into an autoclave with exclusion of air together with 5 g of amorphous zirconium oxide (prepared as in Preparation A above and pretreated for 2 hours at 200° C. with the passage of argon), 80 g of isopropanol (dried using molecular sieve 4 Å) and 20 g of toluene. After flushing several times with nitrogen, the mixture was heated to a temperature of 190° C. at a pressure of 10 bar while stirring at 750 rpm. The pressure rose during the course of this to 25 bar. After 5 hours, the reaction mixture was cooled to room temperature and the amorphous zirconium oxide was separated off. The resultant solution, containing 71.4 percent of a mixture of 75.6 percent nitrochromene and 24.4 percent of aminochromene according to GC was introduced into an autoclave together with 0.4 g of a palladium-on-carbon catalyst (5 percent Pd/C). After flushing several times with nitrogen and then with hydrogen, the mixture was stirred at 750 rpm at a hydrogen pressure of 8 bar and at room temperature (24° to 27° C.) for 1 hour. The reaction mixture was then freed from the catalyst and the solvent was evaporated. The crude product (1.8 g) contained the title product in a yield of 75.1 percent.

What is claimed is:

1. A process for the preparation of a 6-hydroxy-2,5,7,8-tetraalkyl-2-(4-aminophenoxymethyl)chroman of the formula:

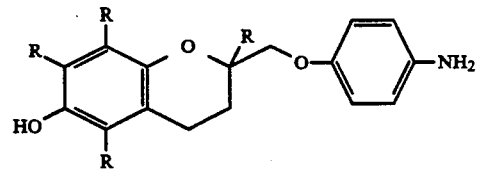

wherein R is a lower alkyl group having 1 to 4 C atoms, characterized in that a 6-hydroxy-2,5,7,8-tetraalkyl-2-(4-nitrophenoxymethyl)chroman-4-one of the formula:

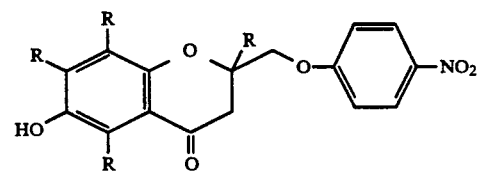

wherein R has the above-stated meaning, is reduced under pressure in the presence of a catalyst system of amorphous zirconium oxide/isopropanol to give a mixture of a 6-hydroxy-2,5,7,8-tetraalkyl-2-(4-aminophenylmethyl)-chrom-3-ene of the formula:

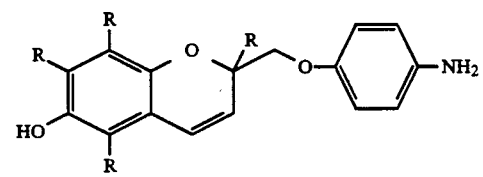

wherein R has the above-stated meaning, and a 6-hydroxy-2,5,7,8-tetraalkyl-2-(4-nitrophenoxymethyl)chrom-3-ene of the formula:

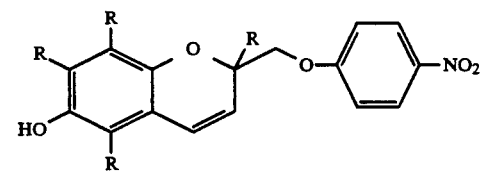

and, in the subsequent step, said mixture is hydrogenated using hydrogen in the presence of a hydrogenation catalyst to give the final product.

2. The process according to claim 1 wherein the reduction in the first step is carried out at a pressure of 1 to 50 bar and a temperature of between 80° and 220° C.

3. The process according to claim 2 wherein the reduction in the first step is carried out at a pressure of 20 to 40 bar and a temperature of between 160° and 200° C.

4. The process according to claim 3 wherein, for the reduction, an amorphous zirconium oxide is employed which is prepared by ammoniacal precipitation of a zirconyl chloride solution and subsequent drying and calcination of the precipitated zirconium oxide.

5. The process according to claim 4 wherein the amorphous zirconium oxide is subjected to a pretreatment in a mobile inert gas atmosphere at a temperature of between 150° to 300° C.

6. The process according to claim 5 wherein a platinum or palladium catalyst applied to an inert support is used as the hydrogenation catalyst.

7. The process according to claim 6 wherein palladium, applied to carbon in an amount from 0.5 to 10 percent, is used.

8. The process according to claim 7 wherein the hydrogenation is carried out at a hydrogen pressure of 1 to 20 bar and a temperature of 20° to 50° C.

9. The process according to claim 1 wherein, for the reduction, an amorphous zirconium oxide is employed which is prepared by ammoniacal precipitation of a zirconyl chloride solution and subsequent drying and calcination of the precipitated zirconium oxide.

10. The process according to claim 9 wherein the amorphous zirconium oxide is subjected to a pretreatment in a mobile inert gas atmosphere at a temperature of between 150° to 300° C.

11. The process according to claim 1 wherein a platinum or palladium catalyst applied to an inert support is used as the hdyrogenation catalyst.

12. The process according to claim 11 wherein palladium, applied to carbon in an amount from 0.5 to 10 percent, is used.

13. The process according to claim 1 wherein the hydrogenation is carried out at a hydrogen pressure of 1 to 20 bar and a temperature of 20° to 50° C.

* * * * *